(12) United States Patent
Schultz et al.

(10) Patent No.: US 9,724,154 B2
(45) Date of Patent: Aug. 8, 2017

(54) IRRIGATED ABLATION CATHETER WITH MULTIPLE SENSORS

(71) Applicant: Biosense Webster (Israel) Ltd., Yokneam (IL)

(72) Inventors: Jeffrey Schultz, Chino, CA (US); Maria J. Duarte, Chino, CA (US); Daniele Ghidoli, Laguna Hills, CA (US); Kelvin Chuu, Hermosa Beach, CA (US); Meir Bar-Tal, Haifa (IL); Jeffrey Clark, Castaic, CA (US); Avri Hazan, Givatayim (IL); Abraham Berger, Givatayim (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 439 days.

(21) Appl. No.: 14/551,229

(22) Filed: Nov. 24, 2014

(65) Prior Publication Data

US 2016/0143690 A1 May 26, 2016

(51) Int. Cl.
*A61B 18/12* (2006.01)
*A61B 18/14* (2006.01)
(Continued)

(52) U.S. Cl.
CPC ............ *A61B 18/1492* (2013.01); *A61B 5/01* (2013.01); *A61B 5/042* (2013.01); *A61B 5/0538* (2013.01); *A61B 2017/00084* (2013.01); *A61B 2018/00029* (2013.01); *A61B 2018/00351* (2013.01); *A61B 2018/00702* (2013.01);
(Continued)

(58) Field of Classification Search
CPC ...... A61B 18/1492; A61B 2017/00084; A61B 2018/00029; A61B 2018/00351; A61B 2018/00702; A61B 2018/00744; A61B 2018/00779; A61B 2018/00791; A61B 2018/00797; A61B 2018/00827; A61B 2018/00875; A61B 2018/00892;
(Continued)

(56) References Cited

U.S. PATENT DOCUMENTS 5,391,199 A 2/1995 Ben-Haim
5,782,828 A 7/1998 Chen et al.
(Continued)

FOREIGN PATENT DOCUMENTS

WO 9605768 2/1996

OTHER PUBLICATIONS

U.S. Appl. No. 13/113,159, filed May 23, 2011.
European Search Report for European Patent Application No. 15195773.5; mailed on Feb. 24, 2016.

*Primary Examiner* — Daniel Fowler

(57) ABSTRACT

Systems and methods are disclosed for providing and using an irrigated ablation catheter. The catheter may include a distal shell electrode having irrigation apertures. An insert disposed within the electrode has protrusions that mate with orifices in the shell of the electrode. Each protrusion has a port communicating with at least one interior lumen in the insert and a sensor is disposed in each port. A support seals the proximal end of the electrode and engages the insert. The plurality of sensors may be used to measure electrical and thermal characteristics surrounding the electrode and may help assess contact between the electrode and tissue and/or determine movement of the electrode during ablation.

20 Claims, 8 Drawing Sheets

(51) Int. Cl.
*A61B 5/01* (2006.01)
*A61B 5/053* (2006.01)
*A61B 5/042* (2006.01)
*A61B 18/00* (2006.01)
*A61B 17/00* (2006.01)
*A61B 90/00* (2016.01)

(52) U.S. Cl.
CPC ............... *A61B 2018/00744* (2013.01); *A61B 2018/00779* (2013.01); *A61B 2018/00791* (2013.01); *A61B 2018/00797* (2013.01); *A61B 2018/00827* (2013.01); *A61B 2018/00875* (2013.01); *A61B 2018/00892* (2013.01); *A61B 2090/065* (2016.02); *A61B 2218/002* (2013.01)

(58) Field of Classification Search
CPC ........ A61B 2090/065; A61B 2218/002; A61B 5/01; A61B 5/042; A61B 5/0538
See application file for complete search history.

(56) References Cited

U.S. PATENT DOCUMENTS

| | | |
|---|---|---|
| 5,849,028 A | 12/1998 | Chen |
| 6,239,724 B1 | 5/2001 | Doron et al. |
| 6,332,089 B1 | 12/2001 | Acker et al. |
| 6,332,881 B1 | 12/2001 | Carner et al. |
| 6,468,260 B1 | 10/2002 | Bumbalough et al. |
| 6,484,118 B1 | 11/2002 | Govari |
| 6,500,167 B1 | 12/2002 | Webster, Jr. |
| 6,522,933 B2 | 2/2003 | Nguyen |
| 6,592,580 B1 | 7/2003 | Stockert |
| 6,592,581 B2 | 7/2003 | Bowe |
| 6,618,612 B1 | 9/2003 | Acker et al. |
| 6,690,963 B2 | 2/2004 | Ben-Haim et al. |
| 8,357,152 B2 | 1/2013 | Govari et al. |
| 8,394,093 B2 | 3/2013 | Wang et al. |
| 8,617,087 B2 | 12/2013 | Schultz |
| 9,050,105 B2 | 6/2015 | Govari et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2005/0070894 A1* | 3/2005 | McClurken ........ A61B 18/1492 606/48 |
| 2009/0093810 A1* | 4/2009 | Subramaniam .... A61B 18/1492 606/41 |
| 2010/0331658 A1 | 12/2010 | Kim et al. |
| 2011/0230799 A1 | 9/2011 | Christian et al. |
| 2013/0123775 A1 | 5/2013 | Grunewald et al. |
| 2014/0276052 A1 | 9/2014 | Rankin |
| 2014/0276759 A1 | 9/2014 | Kim et al. |

\* cited by examiner

IRRIGATED ABLATION CATHETER WITH MULTIPLE SENSORS

FIELD OF THE PRESENT DISCLOSURE

This disclosure relates generally to methods and devices for percutaneous medical treatment, and specifically to catheters, in particular, irrigated ablation catheters. More particularly, this disclosure relates to irrigated ablation catheters designs that support and stabilize micro-elements for accurate thermal and/or electrical sensing properties while providing reduced interference with irrigation of the ablation electrode.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In such procedures, a reference electrode is typically provided and may be attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue. During this process, heating of the electrode also occurs as a result of conduction from the heated tissue to the electrode itself.

Correspondingly, irrigation of the ablation catheter may provide many benefits including cooling of the electrode and tissue to prevent overheating of tissue that can otherwise cause the formation of char and coagulum and even steam pops. Therefore, an irrigated ablation catheter may include one or more temperature sensors, such as thermocouples, thermistors or the like, to assess tissue temperature during an ablation procedure for avoiding such adverse occurrences. It is desirable that the sensed temperature accurately reflects the real temperature of the tissue and not merely tissue temperature which has been biased by the cooling irrigation fluid from the catheter. Moreover, an irrigated ablation catheter may alternatively or in addition include electrical sensors for multiple purposes, including measuring impedance to help determine lesion size, depth and transmurality, performing mapping functions or assessing tissue contact with the RF electrode.

Further, the distal end of an irrigated ablation catheter is subject to significant spatial and design constraints. Since the catheter gains access via an intravascular route, the overall diameter is limited and must be sufficiently flexible to navigate the tortuous anatomy. There must also be an irrigation conduit system to supply the cooling fluid. The distal end also needs to accommodate the above noted RF electrode, temperature sensors and electrical sensors, and the associated electrical connections as well as other functional components that may be included, such as contact force sensor systems, safety wires or other structures.

Accordingly, it would be desirable to provide an irrigated ablation catheter that has one or more temperature and/or electrical sensors positioned at the distal end. It is also desirable to reduce interference between such elements and the irrigation system. For example, it would be desirable to provide the sensors in a manner that increases the surface area of the RF electrode exposed to the irrigation fluid. Likewise, it would be desirable to provide the sensors in a manner that reduces the effect of the irrigation fluid on the measurements. As will be described in the following materials, this disclosure satisfies these and other needs.

SUMMARY

The present disclosure is directed to a catheter having an elongated body, an electrode mounted at a distal end of the elongated body, wherein the electrode is configured as a shell defining an interior space, a plurality of irrigation apertures formed in the shell and communicating with the interior space, an insert disposed within the interior space having a plurality of protrusions configured to mate with a corresponding plurality of orifices in the shell of the electrode, wherein each protrusion extends at least flush with an exterior surface of the electrode and has a port communicating with at least one interior lumen in the insert, a plurality of sensors, wherein each sensor is disposed within one of the ports of the protrusions and a support which forms a fluid tight seal with a proximal end of the electrode and engages a proximal end of the insert to stabilize the insert against rotational motion.

In one aspect, the insert may have at least one longitudinally extending arm with at least one protrusion. Further, the at least one arm may have an interior lumen in communication the port of the at least one protrusion. Still further, the at least one arm may have a plurality of protrusions, such that the interior lumen of the at least one arm is in communication with a plurality of ports. As desired, at least one guide tube may be provided to extend from a through-hole in the support to the interior lumen of the at least one arm.

In one aspect, each protrusion may have a shoulder positioned radially outwards from a surface of the arm, such that the shoulder engages an interior surface of the electrode surrounding the orifice. A minimum separation may be provided between the insert and an interior surface of the electrode, wherein the minimum separation is defined by a distance from the surface of the arm and the shoulder.

In one aspect, the insert may have a plurality of arms. Further, at least one passageway may be provided between the plurality of arms to allow circulation of irrigation fluid within the interior space.

In one aspect, the insert may be formed by an outer portion and an inner portion and wherein the outer portion and the inner portion mate to form the at least one interior lumen. The inner portion may support the outer portion against inward deflection.

In one aspect, at least some of the plurality of sensors may be temperature sensors. In another aspect, at least some of the plurality of sensors may be electrical sensors. Alternatively or in addition, at least one of the plurality of sensors may be a combined temperature and electrical sensor.

This disclosure is also directed to a method for the ablation of a portion of tissue of a patient by an operator. One suitable method includes inserting a catheter into the patient, wherein the catheter has an elongated body, an electrode mounted at a distal end of the elongated body, wherein the electrode is configured as a shell defining an interior space, a plurality of irrigation apertures formed in the shell and communicating with the interior space, an insert disposed within the interior space having a plurality of protrusions configured to mate with a corresponding plurality of orifices in the shell of the electrode, wherein each protrusion extends at least flush with an exterior surface of the electrode and has a port communicating with at least one interior lumen in the insert, a plurality of sensors, wherein each sensor is disposed within one of the ports of the protrusions and a support which forms a fluid tight seal with a proximal end of the electrode and engages a proximal end of the insert to stabilize the insert against rotational motion, then connecting the catheter to a system controller capable of receiving signals from the plurality of sensors and delivering power to the electrode and subsequently controlling the power to the electrode to ablate tissue.

In one aspect, power to the electrode to ablate tissue may be controlled based at least in part on measurements from the plurality of sensors.

In one aspect, irrigation fluid may be delivered to the interior space based at least in part on measurements from the plurality of sensors.

In one aspect, contact of the electrode with tissue may be distinguished from contact of the electrode with blood based at least in part on measurements from the plurality of sensors.

In one aspect, a degree of contact of the electrode with tissue may be estimated based at least in part on measurements from the plurality of sensors.

In one aspect, movement of the electrode during ablation may be determined based at least in part on measurements from the plurality of sensors.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
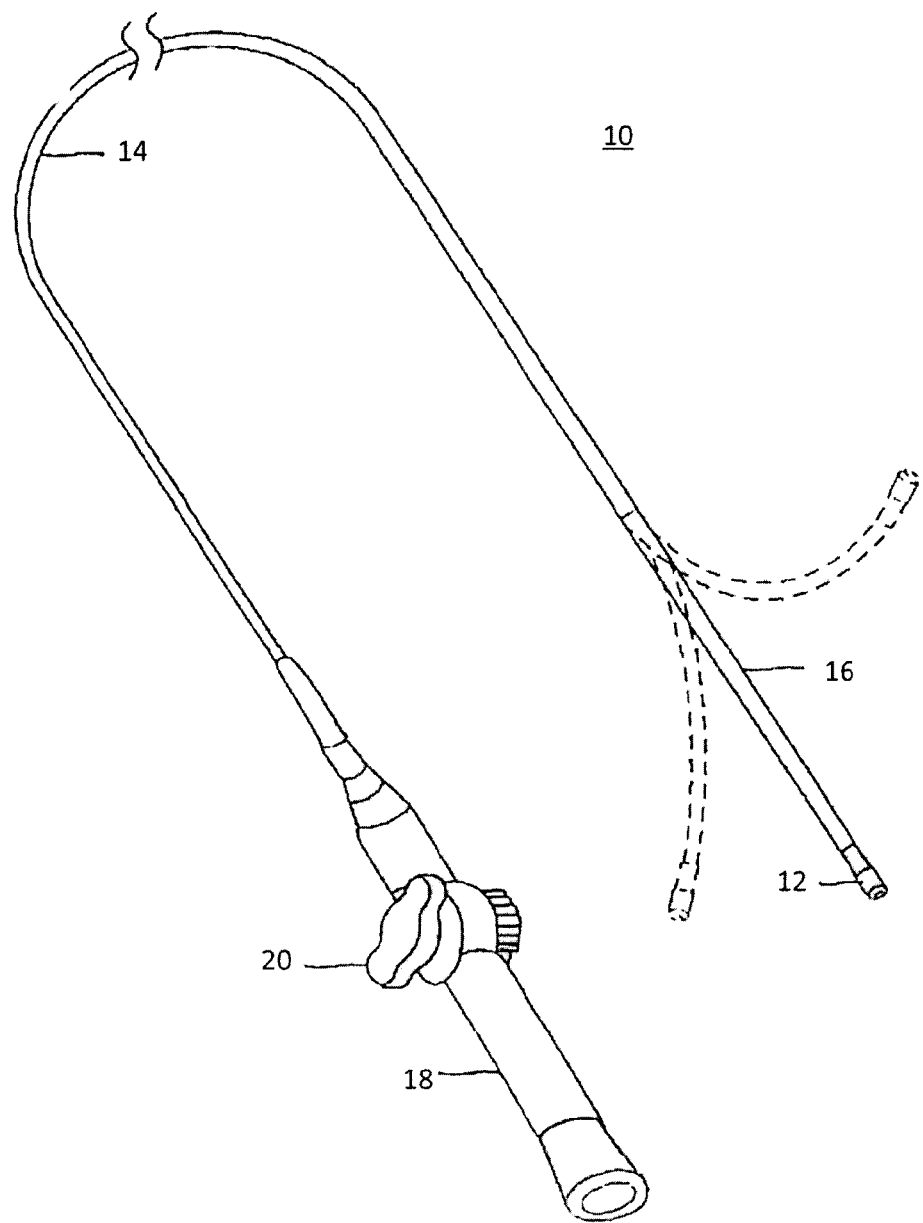
FIG. 1 is a perspective view of a catheter in accordance with an embodiment of the present invention.

As illustrated in FIG. 1, the present disclosure includes irrigated ablation catheter 10 with a distal tip section that includes electrode 12 adapted for contact with target tissue. Catheter 10 according to the disclosed embodiments comprises an elongated body that includes an insertion shaft or catheter body 14 having a longitudinal axis, and an intermediate section 16 distal of the catheter body that optionally may be uni- or bi-directionally deflectable off-axis from the catheter body as indicated. Proximal of catheter body 14 is control handle 18 that allows an operator to maneuver the catheter, including by deflecting intermediate section 14 when a steerable embodiment is employed. For example, control handle 18 may include deflection knob 20 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500, 167, and 6,522,933 and U.S. patent application Ser. No. 12/960,286, filed Dec. 3, 2010, the entire disclosures of which are incorporated herein by reference.

Catheter body 14 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 14 so that, when the control handle 20 is rotated, the intermediate section 16 will rotate in a corresponding manner. Depending upon the intended use, the outer diameter of catheter body 14 may be approximately 8 french, and in some embodiments, may be 7 french. Likewise the thickness of the outer wall of catheter body 14 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm. The length of the intermediate section 16 may correspond to a relatively small portion of the useful length, such as from about 3.5 cm to about 10 cm, and in some embodiments, from about 5 cm to about 6.5 cm.

Figure 2:
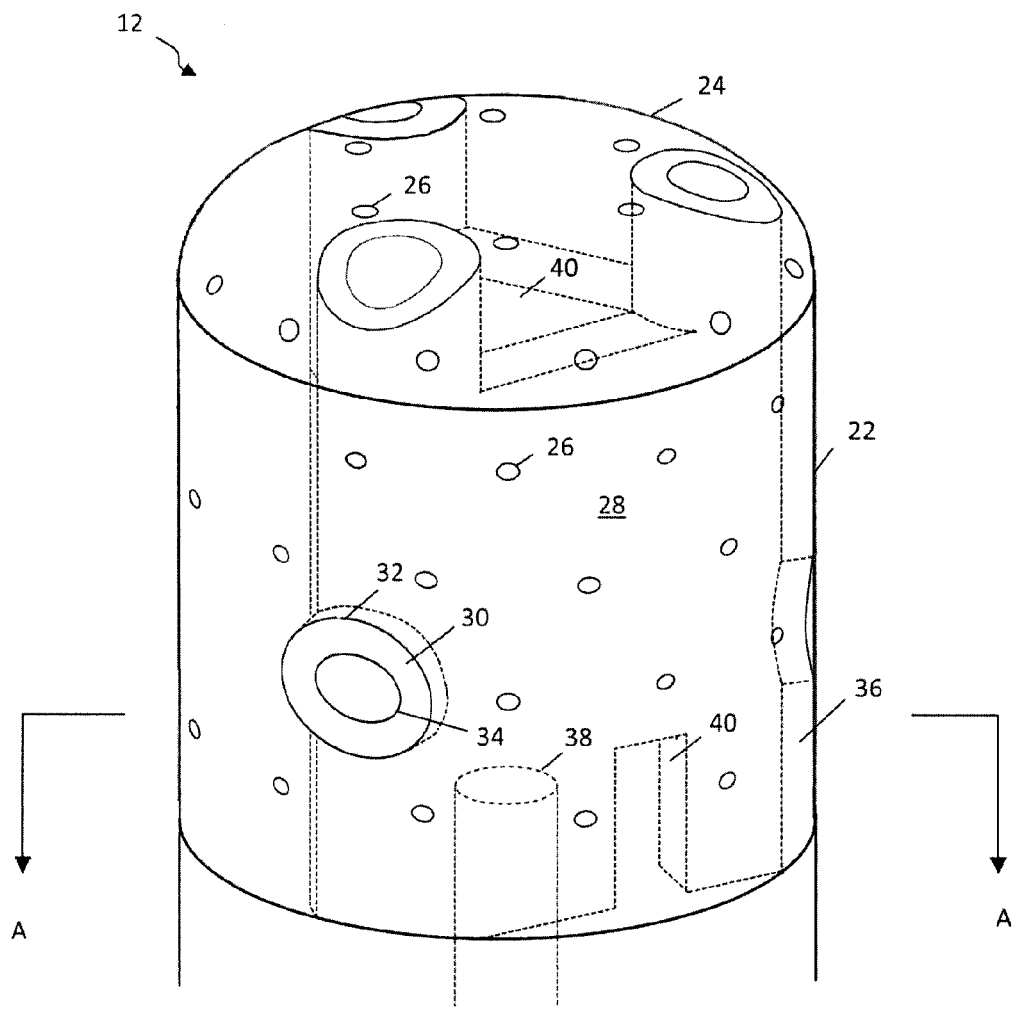
FIG. 2 is a perspective view of an electrode at the distal end of the catheter of FIG. 1 in accordance with an embodiment of the present invention.

Details regarding one embodiment of the distal tip of catheter 10 are illustrated in FIGS. 2-5. Referring now to FIG. 2, electrode 12 is configured as an elongated, generally cylindrical portion 22 and an atraumatic dome-shaped portion 24 at the distal end. The shell of electrode 12 defines an interior cavity that is in fluid communication with a lumen extending the length of catheter body 14 to supply irrigation fluid. A plurality of irrigation apertures 26 are distributed substantially evenly across the surface of electrode 12, through which fluid entering and filling the cavity may exit to outside of the electrode 12, to provide cooling of electrode 12 and the environment adjacent electrode 12 as desired. The shell of electrode 12 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Disposed within electrode 12 is insert 28, schematically shown in phantom, and configured to position a plurality of sensors at desired locations with respect to electrode 12. Insert 28 has multiple protrusions 30 that align with sensor orifices 32 formed in electrode 12. Each protrusion 30 has a port 34 configured to receive a sensor (not shown in this view). Insert 28 may be formed from any suitable material having appropriate electrical and thermal insulating properties, such as PEEK. The number of protrusions 30 may correspond to the number of sensors being employed. In this embodiment, three proximal protrusions are radially spaced by approximately 120 degrees about cylindrical portion 22 and three distal protrusions are radially spaced by approximately 120 degrees about dome-shaped portion 24. This allows insert 28 to have a substantially triangular configuration, such that protrusions 30 are positioned at the apexes of the insert. In other embodiments, other suitable configurations may be employed. Protrusions 30 may be sized to either extend beyond or to be flush with the shell of electrode 12 as desired. For example, protrusions 30 extend from the shell a distance ranging from 0.05-0.3 mm and in one embodiment may extend between about 0.07 and 0.13 mm.

In one aspect, insert 28 may be configured to exhibit reduced contact with electrode 12. For example, in the embodiment shown, insert 28 contacts electrode 12 only through protrusions 30. Accordingly, a minimum separation 36 may be maintained between the body of insert 28 and the inner surface of electrode 12. As will be appreciated, this facilitates circulation and even distribution of irrigation fluid, that may be supplied through lumen 38 (shown in phantom), as well as reducing interference with the exit of the irrigation fluid through apertures 26. Additionally, passageways 40 formed in insert 28 may also facilitate irrigation.

Figure 3:
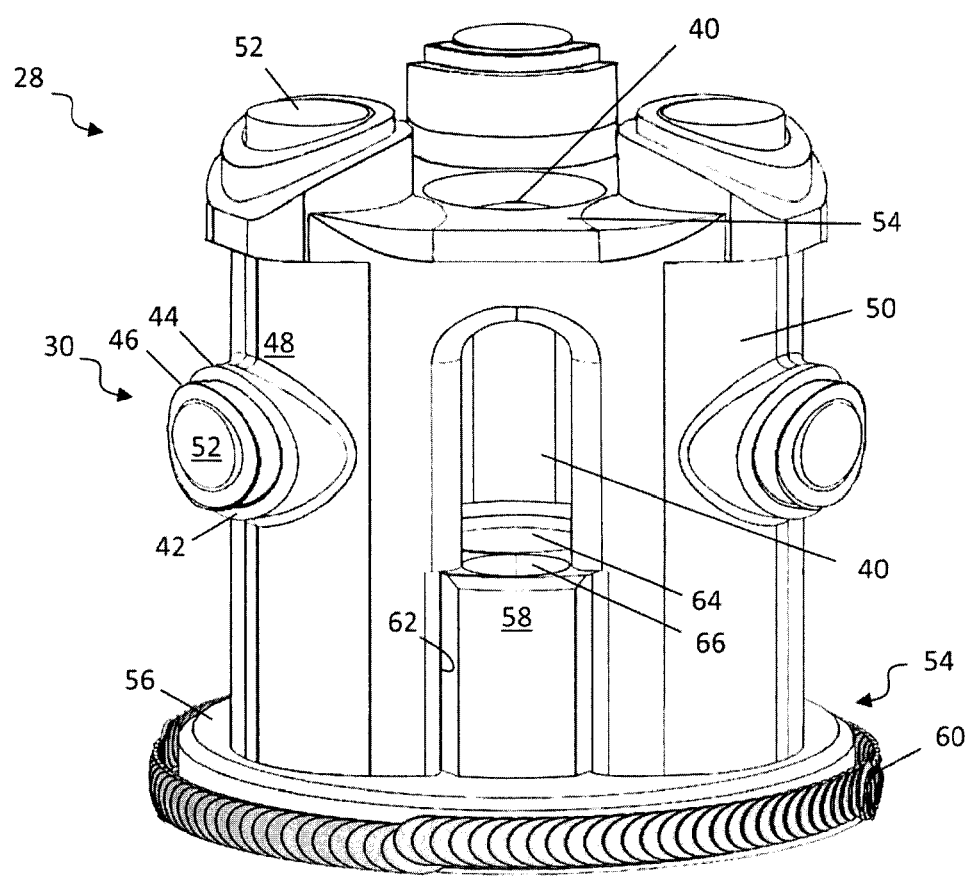
FIG. 3 is an isometric view of an insert accommodating a plurality of sensors within the electrode in accordance with an embodiment of the present invention.

Additional details regarding insert 28 are depicted in FIG. 3. In this view, electrode 12 has been removed to help show aspects of insert 28. As can be seen, protrusions 30 include annular shoulders 42 configured to engage the inner surface of electrode 12. Shoulders 42 may have a surface that is complimentary to the cylindrical portion 22 or dome-shaped portion 24 of electrode 12 as appropriate. The width of shoulders 42 may be defined by the difference between the diameter of a base portion 44 and the diameter of inner portion 46. The diameter of inner portion 46 is sized to mate with sensor orifices 32 (shown in FIG. 2) in electrode 12. Further, the depth of inner portion 12, together with the thickness of the shell of electrode 12 results in protrusions 30 that either extend outward from or are flush with the outer surface of electrode 12. Similarly, annular shoulder 42 extends radially outward from the surface of insert 28, such that the depth of base portion 44 establishes the minimum separation 36 shown in FIG. 2 between the inner surface of electrode 12 and surface 48 on the body of insert 28.

In this embodiment, insert 28 includes three longitudinally extending arms 50, each having a hollow interior portion that communicates with ports 34 to allow routing of leads and wires to sensors 52. Arms 50 are connected at distal crown portion 54. Passageways 40 as described above may be formed between arms 50 as well as by a central opening in crown portion 54. Depending on the intended use and the number of sensors being provided, the configuration of insert 28 may be adapted as desired, such as by featuring two or four arms, for example. In one aspect, each arm 50 may include at least two protrusions 30 to accommodate at least two sensors, such as one proximal and one distal.

Sensors 52 may be any combination of temperature sensors, e.g., thermistor, thermocouple, fluoroptic probe, and the like, or electrical sensors, e.g., micro-electrodes. Any temperature sensor junctions located at or near the end of protrusions 30 and may be potted with a thermally conductive adhesive. Any wires or leads associated with sensors 52 may be routed through arms 50 and ports 34 as appropriate. As will be appreciated, this configuration isolates sensors 52 from electrode 12 and the irrigation fluid. In one aspect, insert 28 serves to thermally insulate sensors 52. Accordingly, a more accurate measurement of tissue and environmental temperature may be obtained by reducing biasing from electrode 12 or the circulating irrigation fluid. In another aspect, insert 28 also serves to electrically insulate sensors 52 to allow more accurate measurement. Similarly, any wires and/or leads are also thermally and electrically insulated, as well as being sealed against corrosion from the irrigation fluid. In one aspect, each sensor 52 positioned by a respective protrusion 30 may be configured to sense a plurality of measurements. For example, one or more sensors 52 may function both as a micro-thermistor and a micro-electrode. According to one embodiment, thermistor wires as well as an electrode lead wire may be connected to a shell cap electrode of sensor 52. Each wire may be isolated from each other by any suitable technique, such as by employing a suitable electrically nonconductive and non-thermally insulative material to fill the interior of arm 50 after placement of sensor 52.

Figure 5:
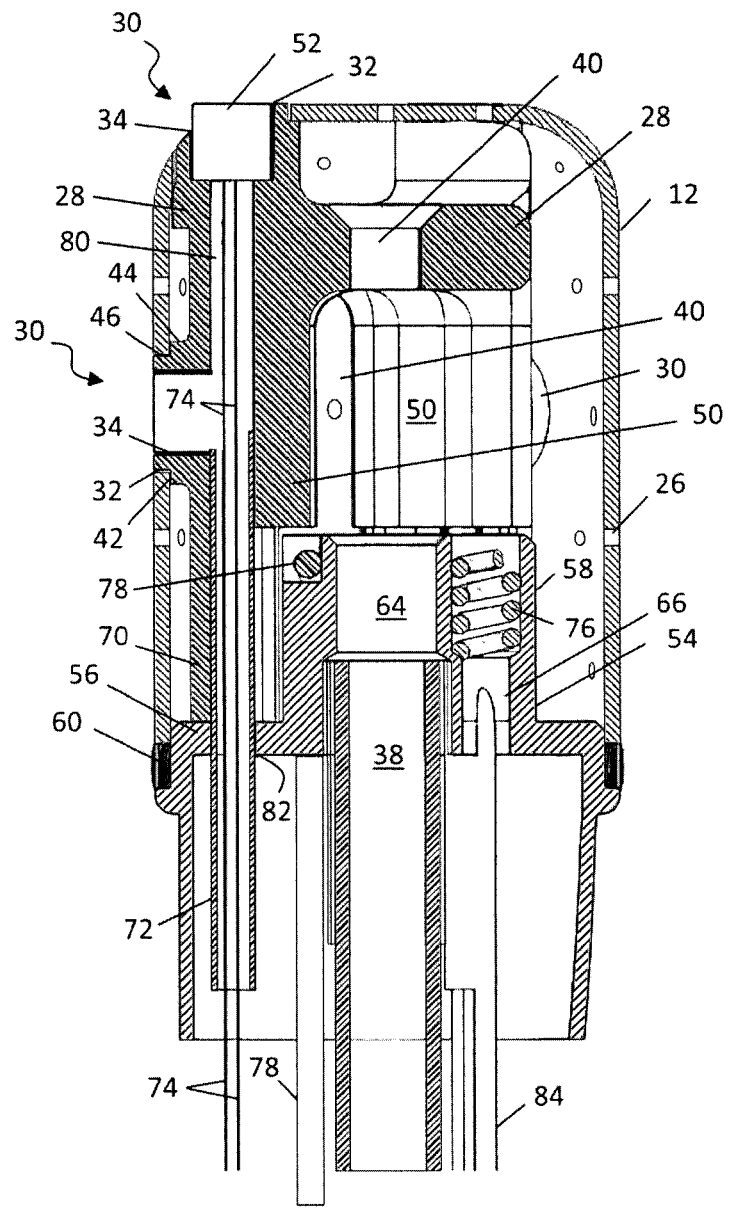
FIG. 5 is a cross-sectional view of the distal end of the catheter, taken at line B-B of FIG. 4, in accordance with an embodiment of the present invention.

Insert 28 is stabilized within electrode 12 by support 54, which includes a disc-shaped base 56 and a distally projecting key 58. Base 56 may have a diameter corresponding to the inner diameter of electrode 12 and may be secured in any suitable manner, such as by welding 60. Key 58 is configured to fit within recess 62 of insert 28, formed by the proximal portions of arms 50, to stabilize insert 28 against axial rotation and possible displacement of sensors 52. Support 54 may provide a fluid tight seal with electrode 12 while routing leads and wires associated with electrode 12 and sensors 52 and irrigation fluid from lumens extending through catheter body 14. For example, central conduit 64 may be in communication with lumen 38 (shown in FIG. 2), to conduct irrigation fluid to passageways 40, for circulation within the interior of electrode 12 and eventual exit through apertures 26. As shown in FIG. 5 below, through-holes in support 54 may align with the interior of arms 50 to accommodate passage of wires to sensors 52. Support 54 may also include one or more radial conduits 66 (one shown in FIG. 3) to accommodate leads for energizing electrode 12, leads for position sensors, a safety wire to prevent loss of the distal end of catheter 10, or other suitable purposes. Support 54 may be formed of any suitable electrically- and thermally-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Figure 4:
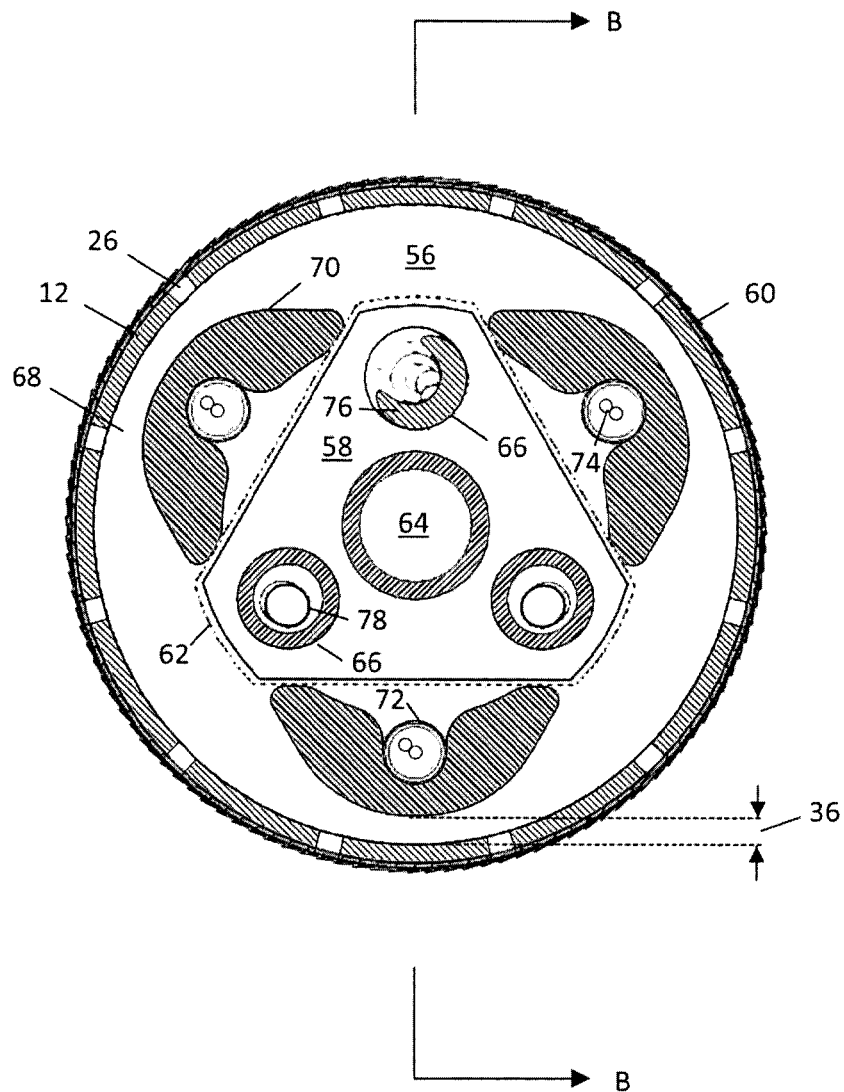
FIG. 4 is a cross-sectional view of the distal end of the catheter, taken at line A-A of FIG. 2, in accordance with an embodiment of the present invention.

Turning now to FIG. 4, an axial cross sectional view taken along line A-A indicated in FIG. 2 is shown. The inner surface of electrode 12 defines irrigation reservoir 68, which may be supplied with irrigation fluid through conduit 64. Proximal portions 70 of arms 50 are positioned apart from the interior surface of electrode 12 by minimum separation 36, defined by the depth of base portion 44 of protrusions 30 as described above. In this embodiment, proximal portions 70 do not have the hollow interior, which is formed distally. Rather, proximal portions 70 receive guide tubes 72 and direct them towards the interiors of arms 50 as shown below in the context of FIG. 5. Guide tubes 72 generally extend from through-holes in support 54 to the interiors of arms 50 to seal, insulate and/or protect wires 74 which connect sensors 52. Guide tubes 72 may be formed of any suitable material that is fluid-tight, electrically-nonconductive, thermally-insulating, and sufficiently flexible, e.g., polyimide, to form a thin-walled tubing. FIG. 4 also illustrates the cooperation between recess 62 (schematically represented by dashed lines) and key 58 of support 54 to stabilize against axial rotation. Key 58 also may engage proximal portions 70 to prevent or reduce deflection inwards of arms 50.

As noted above, support 54 may include one or more radial conduits 66 as desired. In this embodiment, one conduit 66 receives RF coil 76 used to energize electrode 12. Other conduits 66 may be used for any suitable purpose, including routing and/or anchoring safety wire 78 to facilitate retrieval of the electrode assembly or other distal portions of catheter 10 should they become detached during a procedure. Safety wire 78 may be formed from Vectran™ or other suitable materials. In other embodiments, one or more of radial conduits 66 may accommodate electromagnetic position sensors that may be used in conjunction with a mapping system to aid visualization of the placement of the distal end of catheter 10 within a patient's anatomy and/or a force or contact sensing system. Details regarding such aspects may be found in U.S. patent application Ser. Nos. 11/868,733 and 13/424,783, both of which are incorporated herein by reference in their entirety.

Further details of one embodiment of the distal tip of catheter 10 are shown in FIG. 5, which is a longitudinal cross-sectional view taken at line B-B indicated in FIG. 4.

As described above, electrode 12 may be secured to disc-shaped portion 56 of support 54. Insert 28 is positioned within the interior of electrode 12, with protrusions 30 mating with sensor orifices 32. Inner portion 46 of protrusion 30 extends through orifice 32, while shoulder 42 engages the inner surface of electrode 12. As described above, the surfaces of arms 50 may be recessed as defined by the depth of base portion 44 to maintain spacing between insert 28 and electrode 12, thereby improving exposure to irrigation fluid. Guide tube 72 extends between interior lumen 80 of arm 50 and through-hole 82 of support 54 to route wires 74 from sensor 52 (only distal sensor 52 is shown for clarity, with the sensor removed from proximal port 34). Wires and leads 84 may similarly be routed through radial conduit 66 to couple RF coil 76. In this embodiment, safety wire 78 may extend through and be anchored to support 54. Alternatively, safety wire 78 may be anchored in a suitable manner to insert 28.

Figure 6:
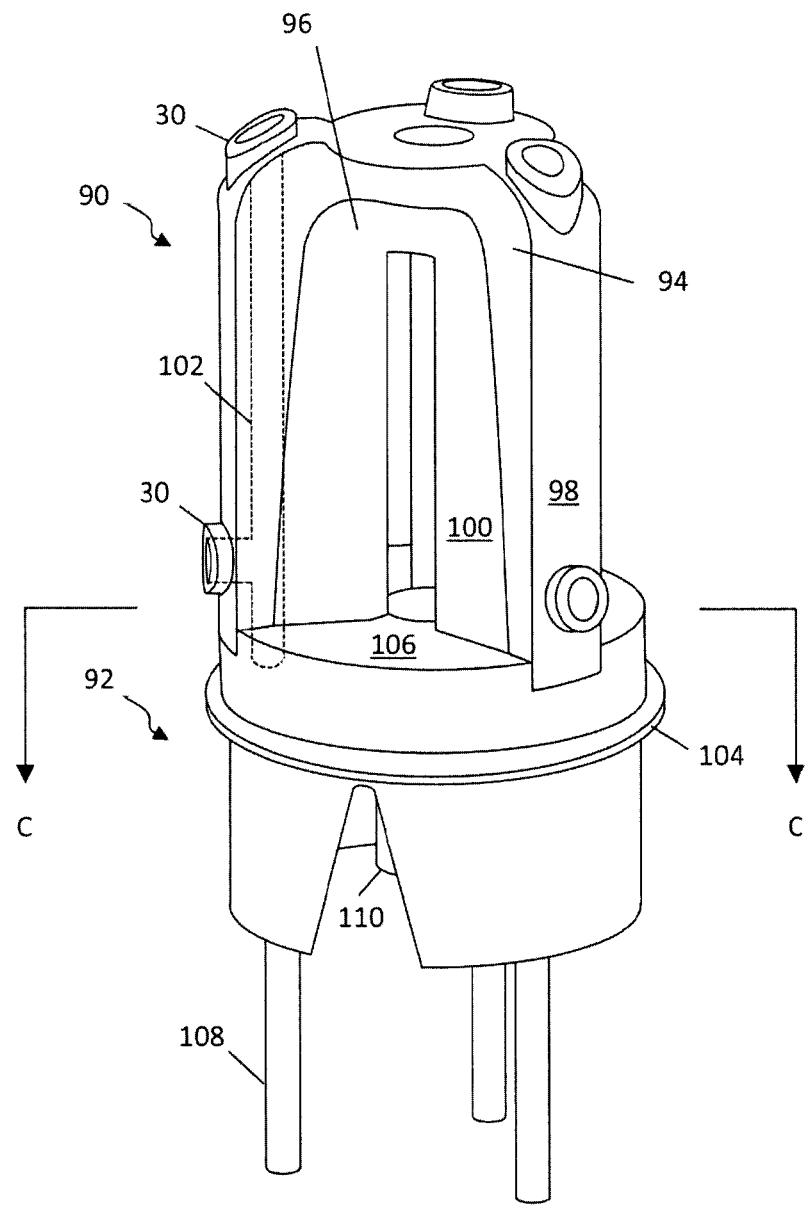
FIG. 6 is an isometric view of another insert accommodating a plurality of sensors within the electrode in accordance with an embodiment of the present invention.

A different embodiment according to the techniques of this disclosure is schematically depicted in FIG. 6. In a similar manner to FIG. 3, electrode 12 has been removed to show details regarding insert 90 and support 92. Insert 90 may be formed from outer portion 94 and inner portion 96. In a similar manner to the other disclosed embodiments, outer portion 94 has a plurality of protrusions 30, each having a port 34 to accommodate a sensor (not shown in this view, but may incorporate any of the features described above). Outer portion 94 may include longitudinally extending arms 98, each having one or more protrusions 30, and inner portion 96 may have corresponding longitudinally extending arms 100. After outer portion 94 is positioned within electrode 12, inner portion 96 may be fit to prevent inward deflection of arms 98. In one aspect, outer arms 98 may be somewhat flexible to facilitate manufacture, so that the arms may be biased inwards when positioned within electrode 12 and then allowed to return to a native configuration when protrusions 30 are properly aligned with sensor orifices 32 in electrode 12, as described above. As shown, this embodiment includes three radial protrusions and three distal protrusions, respectively spaced radially at about 120 degrees with respect to each other. Each protrusion 30 on one arm 98 may communicate with an interior lumen 102 (one shown in phantom), formed when inner portion 96 is mated with outer portion 94.

Support 92 may include disc-shaped portion 104 to be secured to electrode 12 and key 106 to stabilize insert 90 against rotation. Guide tubes 108 may extend through support 92 to the respective interior lumens 102. Central conduit 110 may deliver irrigation fluid to the interior space defined by electrode 12. In this embodiment, the surfaces of arms 98 are configured to rest against the interior surface of electrode 12. Accordingly, contact between insert 90 is confined to longitudinal regions adjacent protrusions 30, leaving substantial portions of the interior surface of electrode 12 exposed to irrigation fluid. In other embodiments, protrusions 30 may include shoulders as described above to increase exposure of the interior surface of electrode 12. Further, spacing between each pair of arms 98 and 100 facilitates circulation of irrigation fluid within the interior of electrode 12. As in the other embodiments of this disclosure, insert 90 may be formed from a suitable electrically- and thermally-insulative material, to help increase the accuracy of sensors disposed within ports 34. Support 92 and electrode 12 to be used in this embodiment may be formed from a suitable electrically- and thermally-conductive material, such as palladium, platinum, gold, iridium and combinations and alloys thereof as described above.

Figure 7:
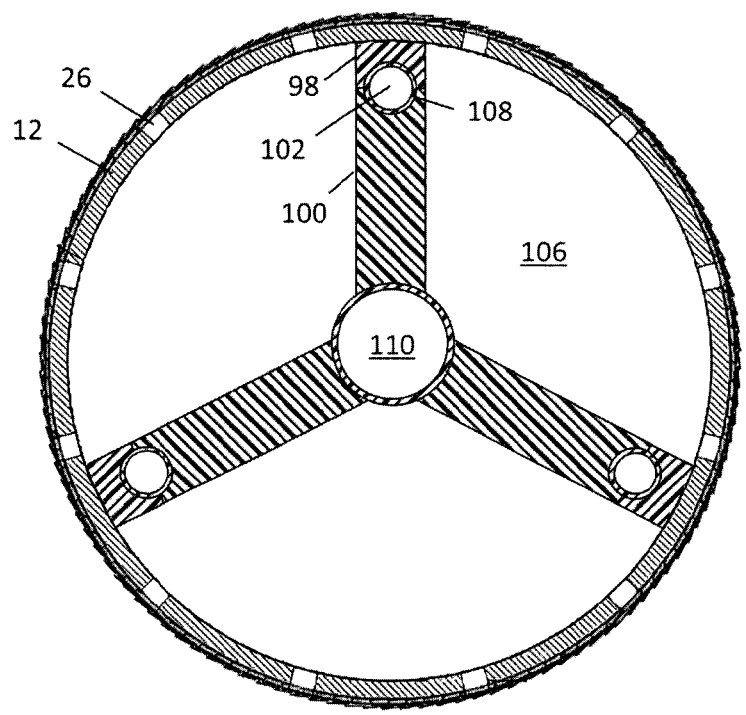
FIG. 7 is a cross-sectional view of the distal end of the catheter, taken at line C-C of FIG. 6, in accordance with an embodiment of the present invention.

An axial cross-sectional view of the embodiment shown in FIG. 6, taken along line C-C, is depicted as FIG. 7. At least a portion of interior lumen 102 may be formed by complimentary surfaces of outer arm 98 and inner arm 100 as shown. As discussed above, portions of key 106 fit between the proximal ends of arm pairs 98 and 100 to stabilize insert 90 against rotational motion.

According to the techniques of this disclosure, protrusions 30 may be used to provide catheter 10 with multiple sensors 52. In one aspect, each sensor may measure temperature and electrical characteristics as described above, to allow for direct monitoring of micro ECG signals and/or micro impedance values using each sensor 52. As will be appreciated, use of either, or both, ECG and impedance provide the ability to determine the contacting tissue at the location of each sensor and help distinguish between blood and tissue. This information may be utilized to confirm sufficient tissue coupling prior to delivery of RF ablation. This may be employed alternatively or in addition to the use of contact force sensors. Additionally, monitoring of electrical feedback from a plurality of sensors 52 distributed across electrode 12 may allow for estimation of a degree of contact between electrode 12 and tissue. For example, the measurements may be used to estimate the percentage of the surface of electrode 12 that is coupled with tissue. In turn, this may be used to better characterize the efficacy of RF delivery by determining what portion of the energy is delivered to tissue as compared to the surrounding blood.

In another aspect, the array of sensors 52 according to the techniques of this disclosure may provide improved temperature response to facilitate determination of catheter movement. As will be appreciated, dragging catheter 10 along tissue may result in frequent rise and fall of temperature response from tissue contacting sensors 52. For example, ablations at a first position followed by movement to a new location may correspond to temperature increase during RF delivery followed by an abrupt decrease in interface temperature at the time of movement, and then by a temperature increase when RF delivery occurs at the new location. Consequently, the ability to quickly detect catheter movement using sensed temperature in this manner may allow for lesion assessment algorithms to "reset" mid ablation and account for detected movement.

In comparison to conventional RF ablation catheters, the techniques of this disclosure represent notable benefits. Prior to ablation, tissue and blood are at a similar temperature preventing use of temperature sensors from being utilized to determine contact, or more specifically areas of an electrode in contact. Contact force catheters are capable of demonstrating contact with tissue but do not provide an indication as to how much of the electrode is in contact with tissue. Further, such conventional contact force technologies may provide information regarding the contact with tissue. However, they do not provide an indication of movement during RF delivery by using the temperature sensing described above. The use of protrusions 30 to accommodate multiple sensors 52 provides sufficient resolution and response time to indicate ablation site movement.

Figure 8:
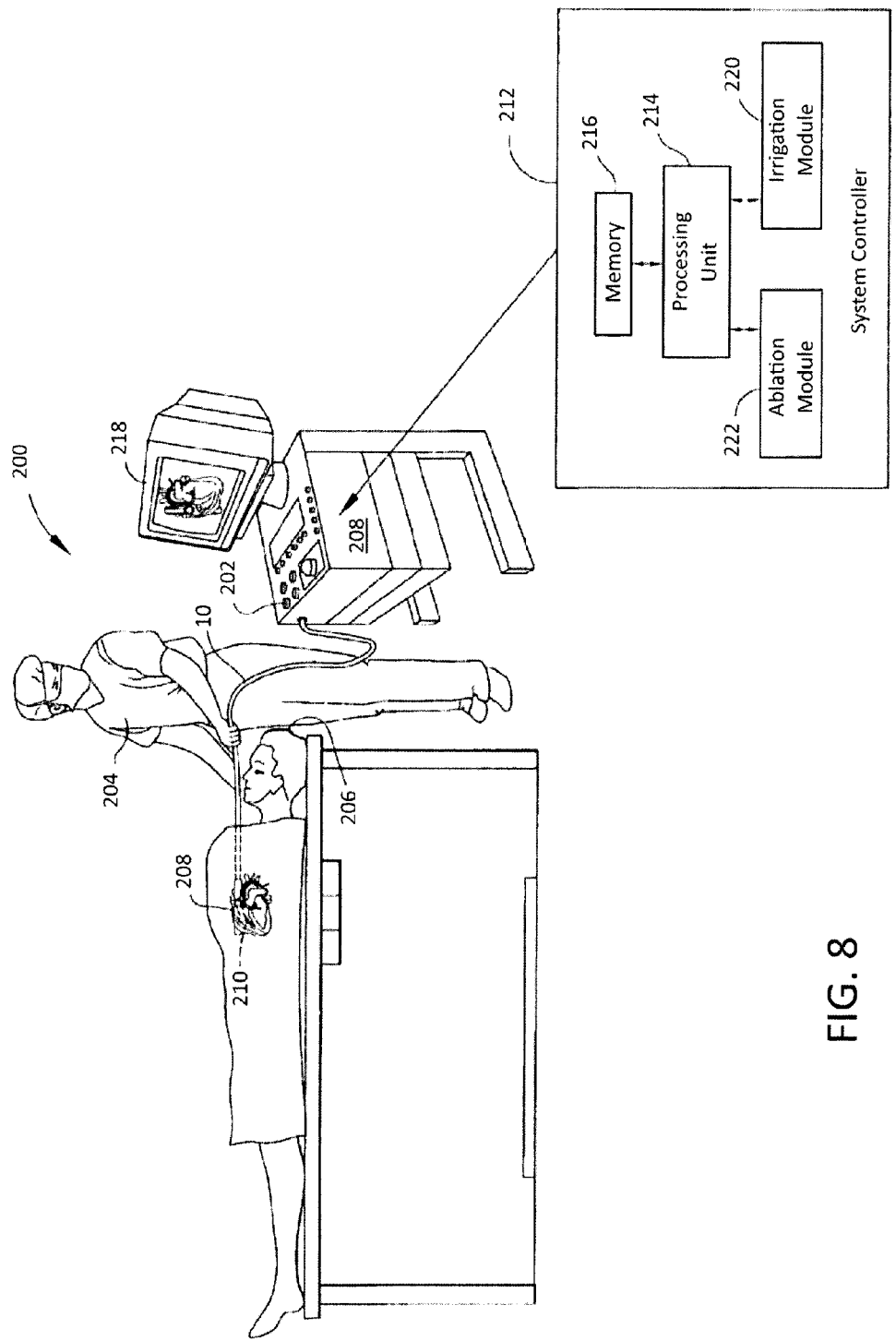
FIG. 8 is a schematic view of an ablation system in accordance with an embodiment of the present invention.

Use of catheter 10 in an ablation procedure may follow techniques known to those of skill in the art. FIG. 8 is a schematic, pictorial illustration of a system 200 for renal and/or cardiac catheterization and ablation, in accordance with an embodiment of the present invention. System 200 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 and a control and/or ablation console 202. An operator 204, such as a cardiologist, electrophysiologist or interventional radiologist, inserts ablation catheter 10 into and through the body of a patient 206, such as through a femoral or radial access approach, so that a distal end of catheter 10, in particular, electrode 12, engages tissue at a desired location or locations, such as a chamber of heart 208 of patient 206. Catheter 10 is typically connected by a suitable connector at its proximal end to console 202. Console 202 comprises a RF generator 208, which supplies high-frequency electrical energy via the catheter for ablating tissue 210 at the locations engaged by electrode 12.

Console 202 may also use magnetic position sensing to determine position coordinates of the distal end of catheter 10 inside the body of the patient 206. For this purpose, a driver circuit in console 202 drives field generators to generate magnetic fields within the body of patient 206. Typically, the field generators comprise coils, which are placed below the patient's torso at known positions external to the patient. These coils generate magnetic fields in a predefined working volume that contains the area of interest. A magnetic field sensor within distal end of catheter 10, such as position sensor 78, generates electrical signals in response to these magnetic fields. A signal processor in console 202 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 202 may include system controller 212, comprising a processing unit 216 communicating with a memory 214, wherein is stored software for operation of system 200. Controller 212 may be an industry standard personal computer comprising a general purpose computer processing unit. However, in some embodiments, at least some of the functions of the controller are performed using custom designed application specific integrated circuits (ASICs) or a field programmable gate array (FPGA). Controller 212 is typically operated by the operator 204 using suitable input peripherals and a graphic user interface (GUI) 218 which enable the operator to set parameters of the system 200. GUI 218 typically also displays results of the procedure to the operator. The software in memory 214 may be downloaded to the controller in electronic form, over a network, for example. Alternatively or additionally, the software may be provided on non-transitory tangible media such as optical, magnetic or electronic storage media. In some embodiments, one or more position sensors may send signals to console 202 to provide an indication of the pressure on electrode 12. Signals from wires 74 may be provided to system controller 212 to obtain measurements from sensors 52. Such signals may be used to provide impedance and/or ECG readings at the location corresponding to sensor 52. Similarly, such signals may be used to provide a temperature reading at the location of sensor 52.

Typically, during an ablation, heat is generated by the RF energy in the tissue of the patient to effect the ablation and some of this heat is reflected to the electrode 12 causing coagulation at and around the electrode. System 200 irrigates this region through irrigation apertures 26 and the rate of flow of irrigation is controlled by irrigation module 220 and the power (RF energy) sent to electrode 12 is controlled by ablation module 222. As noted above, system controller 212 may use electrical and thermal characteristics measured by the plurality of sensors 52 to characterize aspects of the ablation process. For example, measurements from sensors 52 may be used to determine the contacting tissue at the location of each sensor and help distinguish between blood and tissue. Further, the percentage of the surface of electrode 12 that is coupled with tissue may be estimated. As another example, measurements from sensors 52 may help determine movement of electrode 12 during an ablation. Still further, information from sensors 52 may be used to determine the lesion size and depth. Details regarding this aspect may be found in U.S. patent application Ser. No. 13/113,159, entitled "Monitoring Tissue Temperature Using an Irrigated Catheter" the teachings of which is hereby incorporated by reference in its entirety. As yet another example, sensors 52 may also provide intracardiac electrocardiograms to system controller 212, to be used for determining when the tissue site being ablated is no longer conducting arrhythmogenic currents.

Described herein are certain exemplary embodiments. However, one skilled in the art that pertains to the present embodiments will understand that the principles of this disclosure can be extended easily with appropriate modifications to other applications.

What is claimed is:

1. A catheter, comprising:
   an elongated body;
   an electrode mounted at a distal end of the elongated body, wherein the electrode is configured as a shell defining an interior space;
   a plurality of irrigation apertures formed in the shell and communicating with the interior space;
   an insert disposed within the interior space having a plurality of protrusions configured to mate with a corresponding plurality of orifices in the shell of the electrode, wherein each protrusion extends at least flush with an exterior surface of the electrode and has a port communicating with at least one interior lumen in the insert;
   a plurality of sensors, wherein each sensor is disposed within one of the ports of the protrusions; and
   a support which forms a flight tight seal with a proximal-most end of the electrode and engages a proximal end of the insert to stabilize the insert against rotational motion.

2. The catheter of claim 1, wherein the insert comprises at least one longitudinally extending arm with at least one protrusion.

3. The catheter of claim 2, wherein the at least one arm has an interior lumen in communication the port of the at least one protrusion.

4. The catheter of claim 3, wherein the at least one arm has a plurality of protrusions, such that the interior lumen of the at least one arm is in communication with a plurality of ports.

5. The catheter of claim 3, further comprising at least one guide tube extending from a through-hole in the support to the interior lumen of the at least one arm.

6. The catheter of claim 2, wherein each protrusion has a shoulder positioned radially outwards from a surface of the arm, such that the shoulder engages an interior surface of the electrode surrounding the orifice.

7. The catheter of claim 6, further comprising a minimum separation between the insert and an interior surface of the electrode, wherein the minimum separation is defined by a distance from the surface of the arm and the shoulder.

8. The catheter of claim 2, further comprising a plurality of arms.

9. The catheter of claim 8, further comprising at least one passageway between the plurality of arms to allow circulation of irrigation fluid within the interior space.

10. The catheter of claim 3, wherein the insert comprises an outer portion and an inner portion and wherein the outer portion and the inner portion mate to form the at least one interior lumen.

11. The catheter of claim 10, wherein the inner portion supports the outer portion against inward deflection.

12. The catheter of claim 1, wherein at least some of the plurality of sensors are temperature sensors.

13. The catheter of claim 1, wherein at least some of the plurality of sensors are electrical sensors.

14. The catheter of claim 1, wherein at least one of the plurality of sensors is a combined temperature and electrical sensor.

15. A method for the ablation of a portion of tissue of a patient by an operator comprising:
    inserting a catheter into the patient, wherein the catheter comprises:
       an elongated body;
       an electrode mounted at a distal end of the elongated body, wherein the electrode is configured as a shell defining an interior space;
       a plurality of irrigation apertures formed in the shell and communicating with the interior space;
       an insert disposed within the interior space having a plurality of protrusions configured to mate with a corresponding plurality of orifices in the shell of the electrode, wherein each protrusion extends at least flush with an exterior surface of the electrode and has a port communicating with at least one interior lumen in the insert;
       a plurality of sensors, wherein each sensor is disposed within one of the ports of the protrusions; and
       a support which forms a flight tight seal with a proximal-most end of the electrode and engages a proximal end of the insert to stabilize the insert against rotational motion;
    connecting the catheter to a system controller capable of receiving signals from the plurality of sensors and delivering power to the electrode; and
    controlling the power to the electrode to ablate tissue.

16. The method of claim 15, wherein controlling the power to the electrode to ablate tissue is based at least in part on measurements from the plurality of sensors.

17. The method of claim 15, further comprising delivering irrigation fluid to the interior space based at least in part on measurements from the plurality of sensors.

18. The method of claim 15, further comprising distinguishing contact of the electrode with tissue from contact of the electrode with blood based at least in part on measurements from the plurality of sensors.

19. The method of claim 15, further comprising estimating a degree of contact of the electrode with tissue based at least in part on measurements from the plurality of sensors.

20. The method of claim 15, further comprising determining movement of the electrode during ablation based at least in part on measurements from the plurality of sensors.

* * * * *